United States Patent
Morita (10) Patent No.: US 10,987,075 B2
(45) Date of Patent: Apr. 27, 2021

(54) IMAGE PROCESSING APPARATUS, IMAGE PROCESSING METHOD, AND IMAGE PROCESSING PROGRAM

(71) Applicant: FUJIFILM CORPORATION, Tokyo (JP)

(72) Inventor: Junya Morita, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 161 days.

(21) Appl. No.: 16/439,711

(22) Filed: Jun. 13, 2019

(65) Prior Publication Data

US 2019/0388048 A1  Dec. 26, 2019

(30) Foreign Application Priority Data

Jun. 26, 2018  (JP) .............................. JP2018-121080

(51) Int. Cl.
*A61B 6/00* (2006.01)
*G06T 7/00* (2017.01)

(52) U.S. Cl.
CPC ............ *A61B 6/502* (2013.01); *A61B 6/5294* (2013.01); *G06T 7/0012* (2013.01); *G06T 2207/10116* (2013.01); *G06T 2207/30068* (2013.01)

(58) Field of Classification Search
CPC ..... A61B 6/0414; A61B 6/502; A61B 6/5205; A61B 6/5294; G06T 7/0012; G06T 2207/10116; G06T 2207/30068
See application file for complete search history.

(56) References Cited

U.S. PATENT DOCUMENTS

| | | | | |
|---|---|---|---|---|
| 2003/0095624 A1* | 5/2003 | Eberhard | ............... | A61B 6/502 378/37 |
| 2005/0078792 A1* | 4/2005 | Strommer | .............. | A61B 6/544 378/96 |
| 2006/0120510 A1* | 6/2006 | Hanke | .................... | A61B 6/502 378/155 |

(Continued)

FOREIGN PATENT DOCUMENTS

| | | |
|---|---|---|
| JP | H11-19077 A | 1/1999 |
| JP | 2009-268726 A | 11/2009 |
| JP | 2010-253245 A | 11/2010 |

OTHER PUBLICATIONS

Van Engeland, S. et al, "Volumetric Breast Density Estimation from Full-field Digital Mammograms", IEEE Transactions on Medical Imaging, IEEE Service Center, Piscataway, NY, US, vol. 25, No. 3, Mar. 1, 2006, p. 273-282.

(Continued)

*Primary Examiner* — Katrina R Fujita
(74) *Attorney, Agent, or Firm* — Solaris Intellectual Property Group, PLLC (57) ABSTRACT

An image processing apparatus includes: an acquisition unit that acquires a radiographic image of a breast and information indicating a thickness of the breast in capture of the radiographic image; and a derivation unit that derives a percentage of mammary glands of a breast image in the radiographic image acquired by the acquisition unit using different methods in a case in which the thickness of the breast is equal to or greater than a predetermined thickness and a case in which the thickness of the breast is less than the predetermined thickness.

10 Claims, 9 Drawing Sheets

(56) References Cited

U.S. PATENT DOCUMENTS

| | | | |
|---|---|---|---|
| 2008/0101537 A1* | 5/2008 | Sendai | A61B 6/542 378/23 |
| 2009/0022273 A1* | 1/2009 | Kashiwagi | A61B 6/544 378/37 |
| 2014/0112434 A1* | 4/2014 | Jang | A61B 6/502 378/37 |
| 2015/0297163 A1 | 10/2015 | Kim et al. | |
| 2017/0042491 A1* | 2/2017 | Yoon | A61B 6/502 |
| 2017/0281108 A1* | 10/2017 | Choi | A61B 6/0414 |
| 2018/0240224 A1* | 8/2018 | Fukuda | G06T 5/50 |

OTHER PUBLICATIONS

Holland, Katharina et al, "Optimization of Volumetric Breast Density Estimation in Digital Mammograms", Physics in Medicine and Biology, Institute of Physics Publishing, Bristol GB, vol. 62, No. 9, Apr. 11, 2017, pp. 3779-3797.

Extended European Search Report dated Nov. 15, 2019, issued in corresponding EP Patent Application No. 19180962.3.

Amano, Takashi et al., "Measurement of Glandular Dose Using Digital Mammogram," Medical Imaging and Information Sciences, vol. 24, No. 1, pp. 6-12, 2007.

\* cited by examiner

IMAGE PROCESSING APPARATUS, IMAGE PROCESSING METHOD, AND IMAGE PROCESSING PROGRAM

CROSS-REFERENCE TO RELATED APPLICATION

This application claims priority under 35 USC 119 from Japanese Patent Application No. 2018-121080 filed Jun. 26, 2018, the disclosure of which is incorporated by reference herein.

BACKGROUND

Technical Field

The present disclosure relates to an image processing apparatus, an image processing method, and an image processing program.

Related Art

In general, an object of interest, such as a breast cancer, in the breast has been diagnosed on the basis of a radiographic image of the breast of a subject captured by a so-called mammography apparatus. However, in the case of the breast with a high percentage of mammary glands, an image of the object of interest in the radiographic image may be hidden by the mammary glands and may be difficult to see. Therefore, a technique has been known which derives the percentage of the mammary glands. For example, "Measurement of Glandular Dose Using Digital Mammogram," Medical Imaging and Information Sciences, Vol. 24, No. 1, pp. 6-12, 2007 discloses a technique that acquires information indicating the height of a compression plate in the capture of a radiographic image and uses the acquired information to calculate the percentage of the mammary glands.

SUMMARY

However, in many cases, an error is included in the thickness of the breast acquired in the capture of the radiographic image. The error included in the thickness of the breast affects the accuracy of deriving the percentage of the mammary glands. As the amount of the error becomes larger, the accuracy of the derived percentage of the mammary glands becomes lower. The influence of the error becomes larger as the thickness of the breast becomes smaller. As a result, there is a concern that the accuracy of the derived percentage of the mammary glands will be reduced.

In the technique disclosed in "Measurement of Glandular Dose Using Digital Mammogram," Medical Imaging and Information Sciences, Vol. 24, No. 1, pp. 6-12, 2007, as described above, there is a concern that the accuracy of the derived percentage of the mammary glands will be reduced.

The present disclosure has been made in view of the above-mentioned problems and an object of the present disclosure is to provide an image processing apparatus, an image processing method, and an image processing program that can derive the percentage of the mammary glands with high accuracy regardless of the thickness of the breast.

In order to achieve the object, according to a first aspect of the present disclosure, there is provided an image processing apparatus comprising: an acquisition unit that acquires a radiographic image of a breast and information indicating a thickness of the breast in capture of the radiographic image; and a derivation unit that derives a percentage of mammary glands of a breast image in the radiographic image acquired by the acquisition unit using different methods in a case in which the thickness of the breast is equal to or greater than a predetermined thickness and a case in which the thickness of the breast is less than the predetermined thickness.

According to a second aspect of the present disclosure, in the image processing apparatus according to the first aspect, in a case in which the thickness of the breast is equal to or greater than the predetermined thickness, the derivation unit may derive the percentage of the mammary glands of the breast image on the basis of the thickness of the breast.

According to a third aspect of the present disclosure, in the image processing apparatus according to the first or second aspect, in a case in which the thickness of the breast is less the predetermined thickness, the derivation unit may derive the percentage of the mammary glands of the breast image on the basis of an amount of incident radiation on a fat tissue pixel obtained by a portion of the breast which is estimated to be composed of only fat tissues in the radiographic image or an amount of incident radiation on a mammary gland tissue pixel obtained by a portion of the breast which is estimated to be composed of only mammary gland tissues in the radiographic image.

According to a fourth aspect of the present disclosure, in the image processing apparatus according to the third aspect, in a case in which a type of the breast is a high-concentration type, the derivation unit may derive the percentage of the mammary glands of the breast image on the basis of the amount of incident radiation on the mammary gland tissue pixel.

According to a fifth aspect of the present disclosure, in the image processing apparatus according to the third or fourth aspect, in a case in which the type of the breast is a type other than the high-concentration type, the derivation unit may derive the percentage of the mammary glands of the breast image on the basis of the amount of incident radiation on the fat tissue pixel.

According to a sixth aspect of the present disclosure, in the image processing apparatus according to any one of the first to fifth aspects, the predetermined thickness may be a thickness corresponding to an error which is included in a measured value of the thickness of the breast.

According to a seventh aspect of the present disclosure, in the image processing apparatus according to any one of the first to sixth aspects, the information indicating the thickness of the breast may be information indicating a height of a compression plate that compresses the breast in a case in which an image of the breast is captured.

According to an eighth aspect of the present disclosure, in the image processing apparatus according to any one of the first to seventh aspects, the derivation unit may derive the percentage of the mammary glands for each pixel.

According to a ninth aspect of the present disclosure, there is provided an image processing method comprising: acquiring a radiographic image of a breast and information indicating a thickness of the breast in capture of the radiographic image; and deriving a percentage of mammary glands of a breast image in the radiographic image using different methods in a case in which the thickness of the breast is equal to or greater than a predetermined thickness and a case in which the thickness of the breast is less than the predetermined thickness.

According to a tenth aspect of the present disclosure, there is provided an image processing program that causes a computer to perform: acquiring a radiographic image of a breast and information indicating a thickness of the breast in capture of the radiographic image; and deriving a percentage of mammary glands of a breast image in the radiographic image using different methods in a case in which the thickness of the breast is equal to or greater than a predetermined thickness and a case in which the thickness of the breast is less than the predetermined thickness.

According to the present disclosure, it is possible to derive the percentage of the mammary glands with high accuracy regardless of the thickness of the breast even in a case in which the breast is a high-concentration type.

BRIEF DESCRIPTION OF THE DRAWINGS

Exemplary Embodiments of the present invention will be described in detail with reference to the following figures, wherein.

DETAILED DESCRIPTION

Hereinafter, embodiments of the invention will be described in detail with reference to the drawings. The embodiments do not limit the invention.

Figure 1:
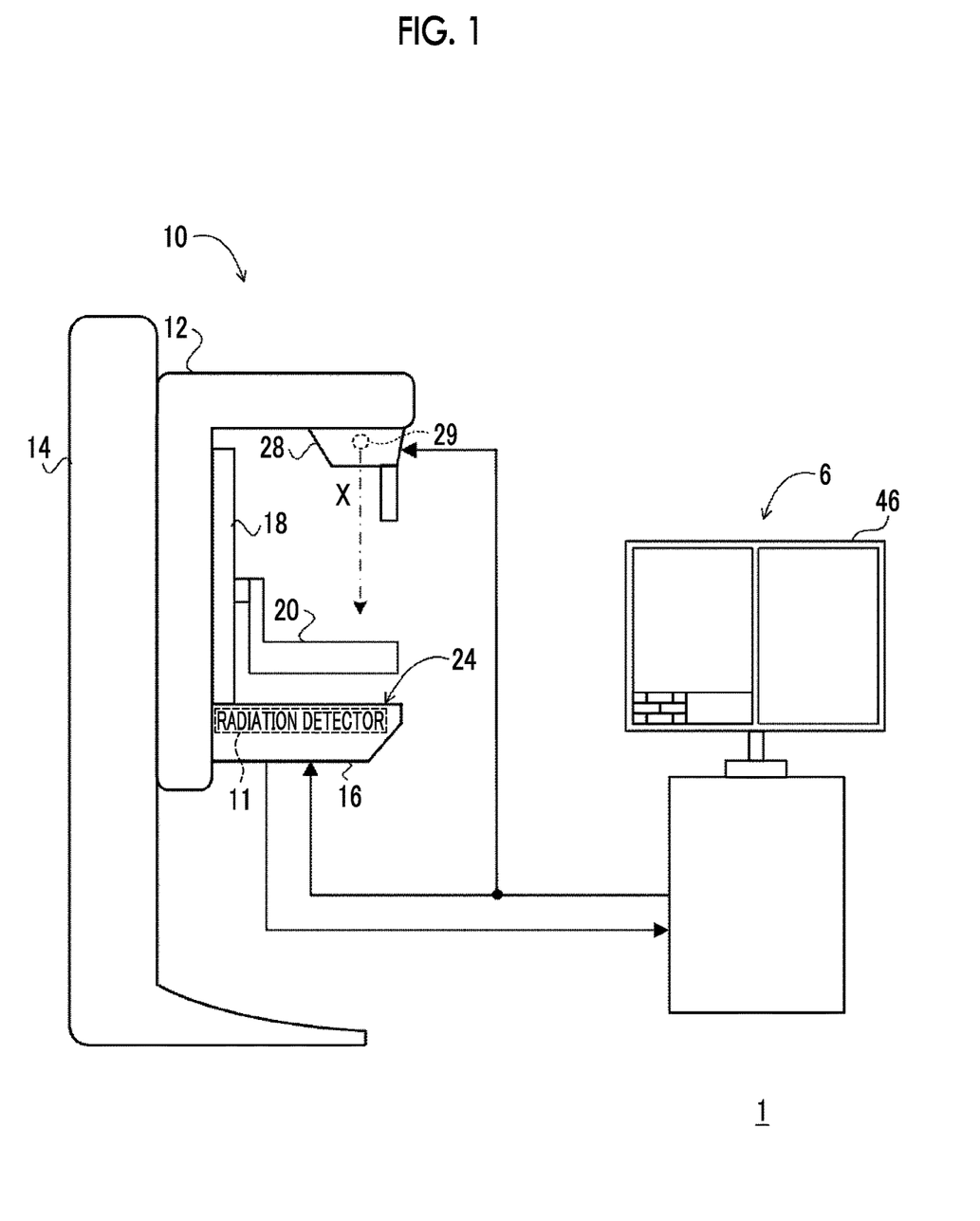
FIG. 1 is a diagram illustrating an example of the overall configuration of a radiography system according to an embodiment.

First, an example of the overall configuration of a radiography system according to this embodiment will be described. FIG. 1 is a configuration diagram illustrating an example of the overall configuration of a radiography system 1 according to this embodiment.

The radiography system 1 according to this embodiment has a function of capturing radiographic images in response to an operation of a user, such as a doctor or a radiology technician, on the basis of a command (imaging order) input from an external system (for example, a radiology information system (RIS)) through a console 6.

Figure 2:
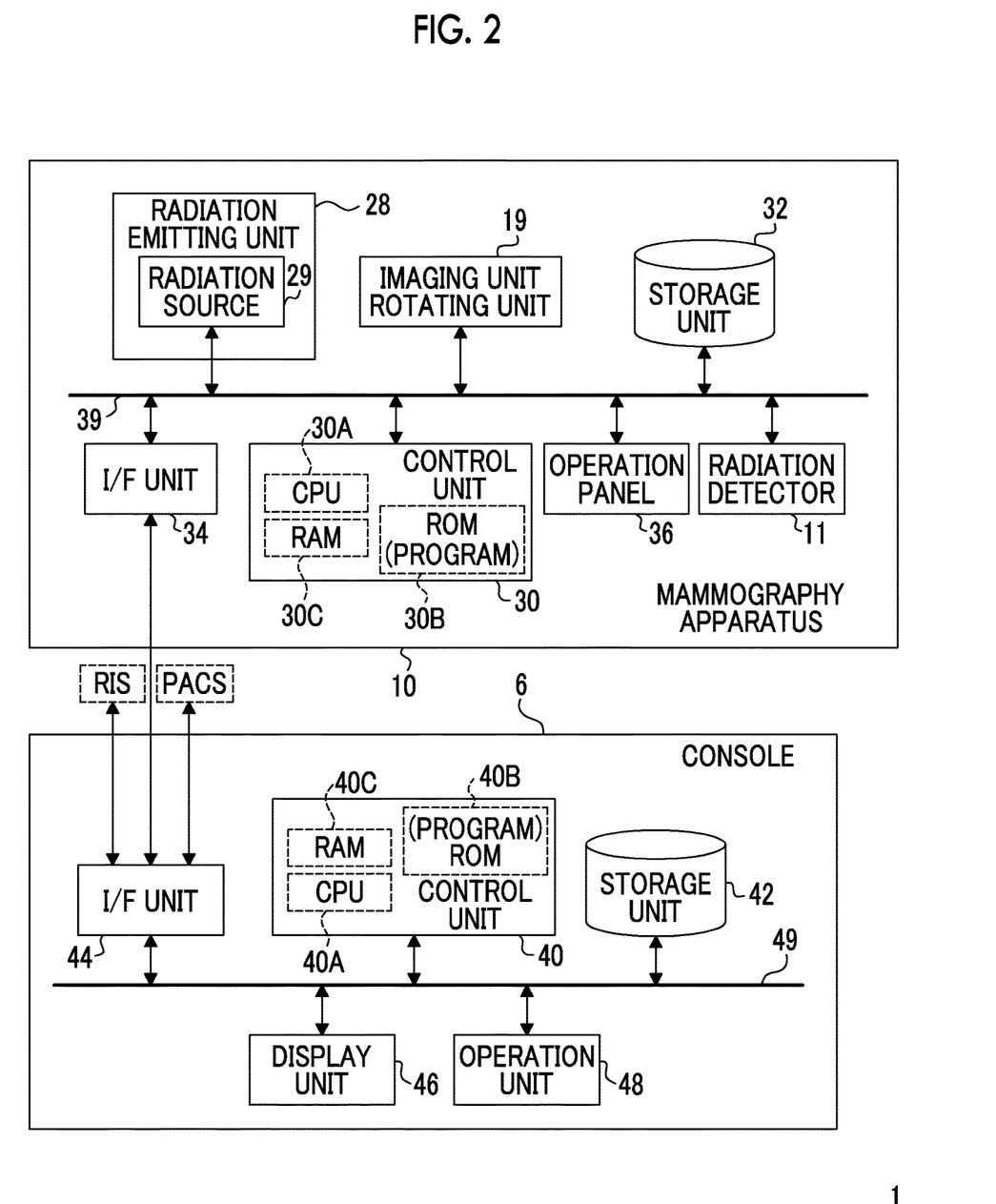
FIG. 2 is a block diagram illustrating an example of the configuration of a console and a mammography apparatus according to the embodiment.

As illustrated in FIG. 1, the radiography system 1 according to this embodiment comprises the console 6 and a mammography apparatus 10. FIG. 2 is a block diagram illustrating an example of the configuration of the console 6 and the mammography apparatus 10 according to this embodiment.

The console 6 according to this embodiment has a function of controlling the mammography apparatus 10 using, for example, an imaging order or various kinds of information acquired from an external system through a wireless communication local area network (LAN). The console 6 according to this embodiment is an example of an image processing apparatus according to the present disclosure.

For example, the console 6 according to this embodiment is a server computer. As illustrated in FIG. 2, the console 6 includes a control unit 40, a storage unit 42, an interface (I/F) unit 44, a display unit 46, and an operation unit 48. The control unit 40, the storage unit 42, the I/F unit 44, the display unit 46, and the operation unit 48 are connected to each other through a bus 49, such as a system bus or a control bus, such that they can transmit and receive various kinds of information.

The control unit 40 according to this embodiment controls the overall operation of the console 6. The control unit 40 according to this embodiment includes a central processing unit (CPU) 40A, a read only memory (ROM) 40B, and a random access memory (RAM) 40C. For example, various programs including a mammary gland percentage derivation processing program (which will be described below) executed by the CPU 40A are stored in the ROM 40B in advance. The RAM 40C temporarily stores various kinds of data.

For example, the image data of a radiographic image captured by the mammography apparatus 10 and various other kinds of information are stored in the storage unit 42. Examples of the storage unit 42 include a hard disk drive (HDD) and a solid state drive (SSD). The I/F unit 44 transmits and receives various kinds of information to and from the mammography apparatus 10 or external systems, such as an RIS and a picture archiving and communication system (PACS), using at least one of wireless communication or wired communication.

The display unit 46 displays, for example, information related to imaging and the captured radiographic image. The operation unit 48 is used by a user to input, for example, a command to capture a radiographic image and a command related to image processing for the captured radiographic image. For example, the operation unit 48 may have the form of a keyboard or various types of switches or the form of a touch panel integrated with the display unit 46.

The mammography apparatus 10 according to this embodiment is an apparatus that irradiates the breast of a subject, which is an object, with radiation X (X-rays) to capture the radiographic image of the breast. As illustrated in FIG. 1, the mammography apparatus 10 comprises an imaging unit 12 and a base portion 14 that supports the imaging unit 12.

The imaging unit 12 comprises an imaging table 16 having a planar imaging surface 24 that come into contact with the breast of the subject, a compression plate 20 that compresses the breast against the imaging surface 24 of the imaging table 16, and a holding portion 18 that supports the imaging table 16 and the compression plate 20. In addition, a member that transmits the radiation X is used as the compression plate 20. In addition, the imaging unit 12 according to this embodiment is rotated by an imaging unit rotating unit 19 in a state in which the imaging unit 12 holds the imaging table 16, which will be described in detail below.

The holding portion 18 supports the imaging table 16 and a radiation source 29 such that the imaging surface 24 and the radiation source 29 are separated by a predetermined distance. In addition, the holding portion 18 holds the compression plate 20 such that the compression plate 20 is slid to change the distance between the compression plate 20 and the imaging surface 24.

In a case in which the mammography apparatus 10 captures the radiographic image of the breast of the subject, for example, a user positions the subject and the breast placed on the imaging surface 24 of the imaging table 16 is compressed between the compression plate 20 and the imaging surface 24 and is fixed.

A radiation detector 11 that detects the radiation X transmitted through the breast and the imaging surface 24 is provided in the imaging table 16. A radiographic image is generated on the basis of the radiation X detected by the radiation detector 11. However, the type of radiation detector 11 according to this embodiment is not particularly limited. For example, the radiation detector 11 may be an indirect-conversion-type radiation detector that converts the radiation X into light and converts the converted light into charge or a direct-conversion-type radiation detector that directly converts the radiation X into charge. In this embodiment, image data indicating the radiographic image output from the radiation detector 11 of the mammography apparatus 10 is transmitted to the console 6.

The mammography apparatus 10 according to this embodiment can perform both craniocaudal (CC) imaging in which an imaging direction is a craniocaudal direction and mediolateral-oblique (MLO) imaging in which the imaging direction is a mediolateral-oblique direction for the breast. In the following description, in radiography, the position of the radiation source 29 in a case in which the radiation source 29 emits the radiation X to the imaging table 16 is referred to as an "imaging position".

Figure 3A:
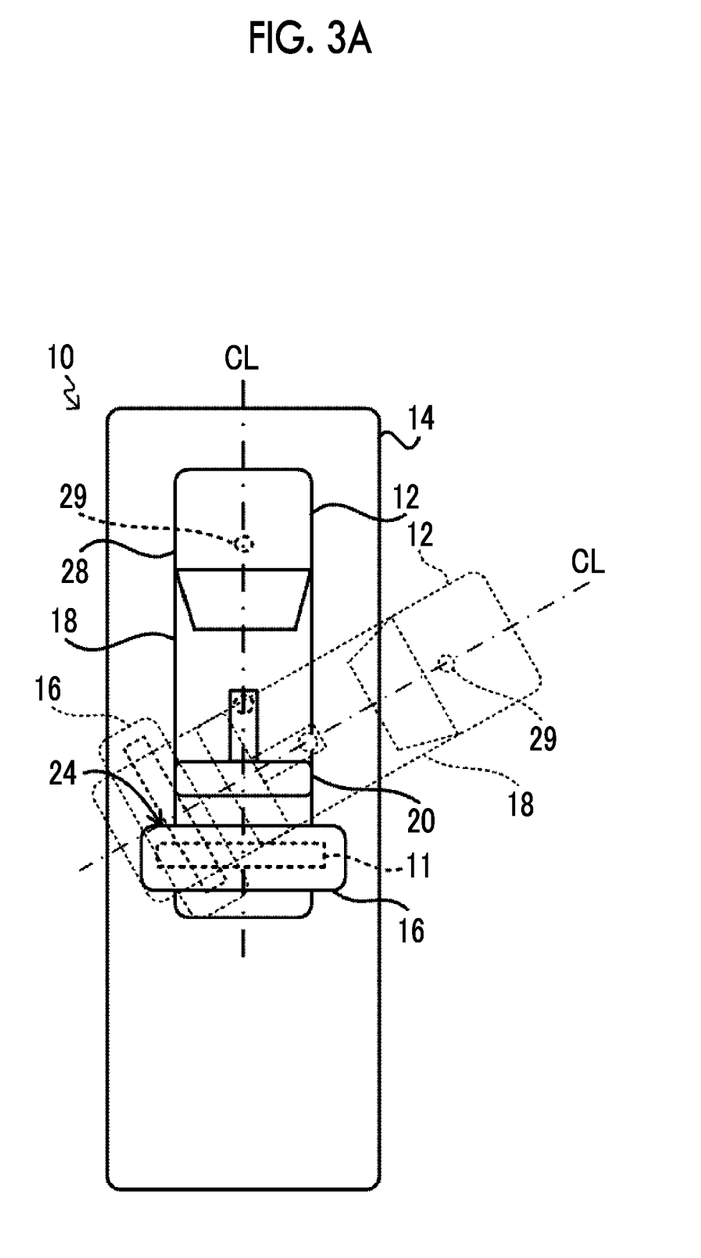
FIG. 3A is a front view illustrating an example of the state of the mammography apparatus in a case in which an image of the left breast of a subject is captured.
Figure 3B:
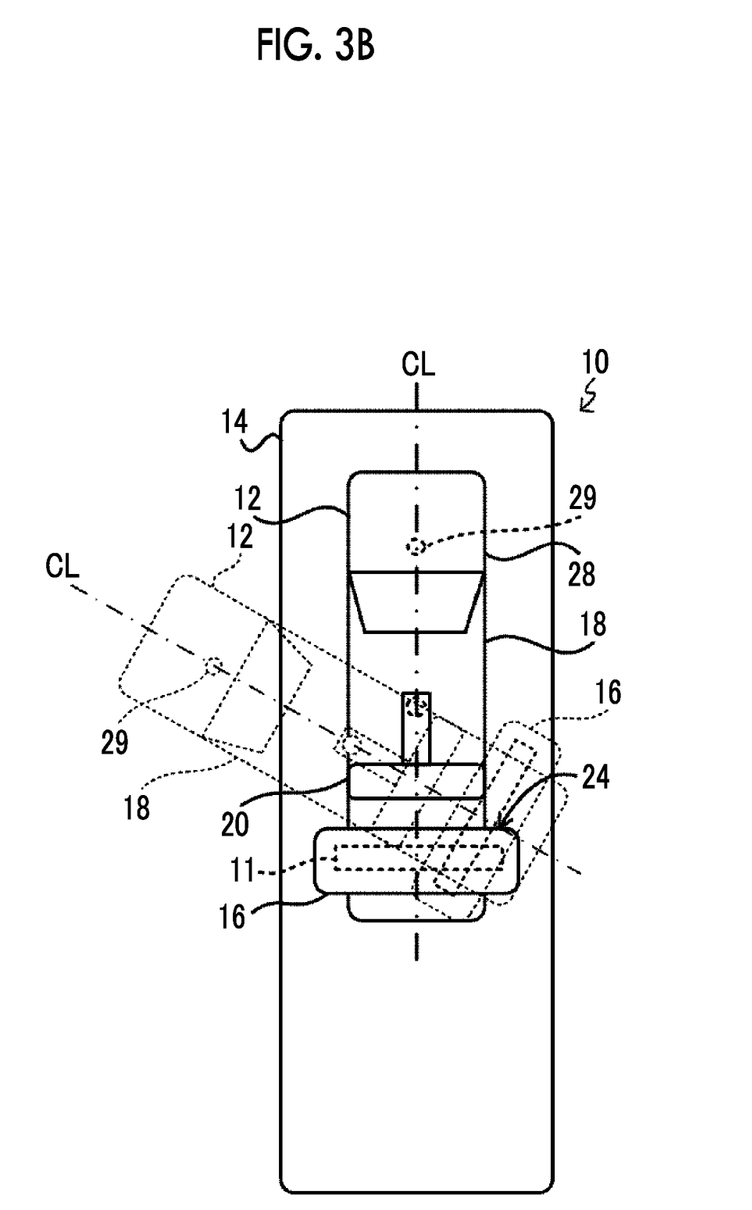
FIG. 3B is a front view illustrating an example of the state of the mammography apparatus in a case in which an image of the right breast of the subject is captured.

In a case in which the CC imaging is performed, the imaging table 16 is adjusted to a state in which the imaging surface 24 faces the upper side (the head of the subject) of the mammography apparatus 10, that is, a state in which a normal direction to the imaging surface 24 is vertical. In this case, the position of the radiation source 29 is adjusted to an imaging position where the radiation source 29 faces the imaging surface 24 of the imaging table 16. Specifically, the position of the radiation source 29 is adjusted to an imaging position where the radiation source 29 is vertical with respect to a normal line CL (see FIGS. 3A and 3B) to the imaging surface 24 (that is, the angle formed between the normal line CL (see FIGS. 3A and 3B) and the radiation source 29 is 0 degrees). Therefore, the radiation X is emitted from the radiation source 29 to the breast in a direction from the head to the foot of the subject and the CC imaging is performed.

In a case in which the MLO imaging is performed, the imaging unit rotating unit 19 adjusts the position of the imaging table 16 to a state in which the imaging surface 24 is rotated to a predetermined angle in the range that is equal to or greater than 45 degrees and less than 90 degrees, as compared to the case in which the CC imaging is performed. Specifically, in a case in which the image of the left breast of the subject is captured, for example, as represented by a dashed line in FIG. 3A, the imaging unit rotating unit 19 rotates the imaging table 16 such that the imaging surface 24 is inclined to the right. In addition, the image of the right breast of the subject is captured, as represented by a dashed line in FIG. 3B, the imaging unit rotating unit 19 rotates the imaging table 16 such that the imaging surface 24 is inclined to the left. Then, the position of the radiation source 29 is adjusted to an imaging position where the radiation source 29 faces the imaging surface 24 of the imaging table 16. Therefore, the radiation X is emitted from the radiation source 29 to the breast in a direction from the center to the outside of the body of the subject (from a part between the breasts to the arm of the subject) and the MLO imaging is performed.

As such, in the mammography apparatus 10 according to this embodiment, in both the CC imaging and the MLO imaging, the radiation source 29 faces the imaging surface 24 at the imaging position. Hereinafter, a radiographic image obtained by the CC imaging is referred to as a "CC image" and a radiographic image obtained by the MLO imaging is referred to as an "MLO image". In addition, in a case in which the CC image and the MLO images are generically referred to, they are simply referred to as "radiographic images".

As illustrated in FIG. 2, the mammography apparatus 10 according to this embodiment comprises the radiation detector 11, the imaging unit rotating unit 19, a radiation emitting unit 28 including the radiation source 29, a control unit 30, a storage unit 32, an I/F unit 34, and an operation panel 36. The radiation detector 11, the imaging unit rotating unit 19, the radiation emitting unit 28, the control unit 30, the storage unit 32, the I/F unit 34, and the operation panel 36 are connected to each other through a bus 39, such as a system bus or a control bus, such that they can transmit and receive various kinds of information.

The control unit 30 according to this embodiment controls the overall operation of the mammography apparatus 10. In addition, in a case in which a radiographic image is captured, the control unit 30 according to this embodiment controls the radiation detector 11 and the radiation emitting unit 28. The control unit 30 according to this embodiment comprises a CPU 30A, a ROM 30B, and a RAM 30C. For example, various programs including a program for controlling the capture of a radiographic image which are executed by the CPU 30A are stored in the ROM 30B in advance. The RAM 30C temporarily stores various kinds of data.

For example, the image data of the radiographic image captured by the radiation detector 11 and various other kinds of information are stored in the storage unit 32. Examples of the storage unit 32 include an HDD and an SSD. The I/F unit 34 transmits and receives various kinds of information to and from the console 6 using wireless communication or wired communication. For example, the operation panel 36 is provided as a plurality of switches in the imaging table 16 of the mammography apparatus 10. In addition, the operation panel 36 may be provided as a touch panel.

Figure 4:
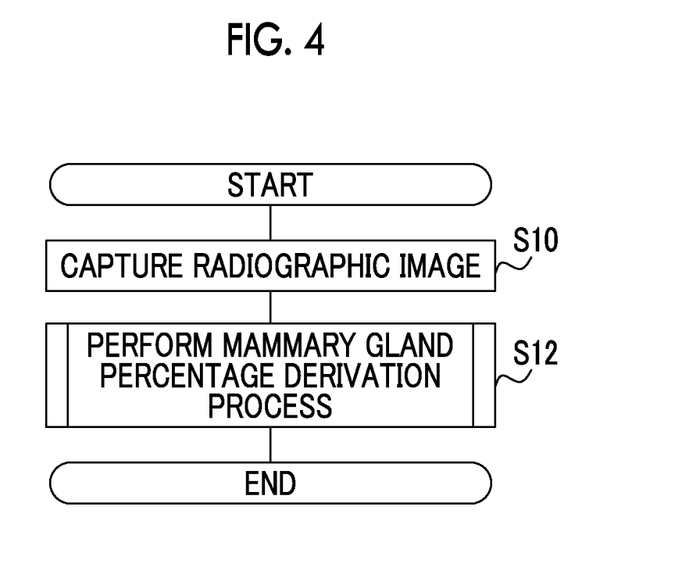
FIG. 4 is a flowchart illustrating an example of the flow of an imaging operation of capturing a radiographic image of the breast of the subject in the entire radiography system according to the embodiment.

Next, the operation of the radiography system 1 according to this embodiment will be described. FIG. 4 is a flowchart illustrating an example of the flow of an imaging operation of capturing the radiographic image of the breast of the subject in the entire radiography system 1 according to this embodiment.

Figure 5:
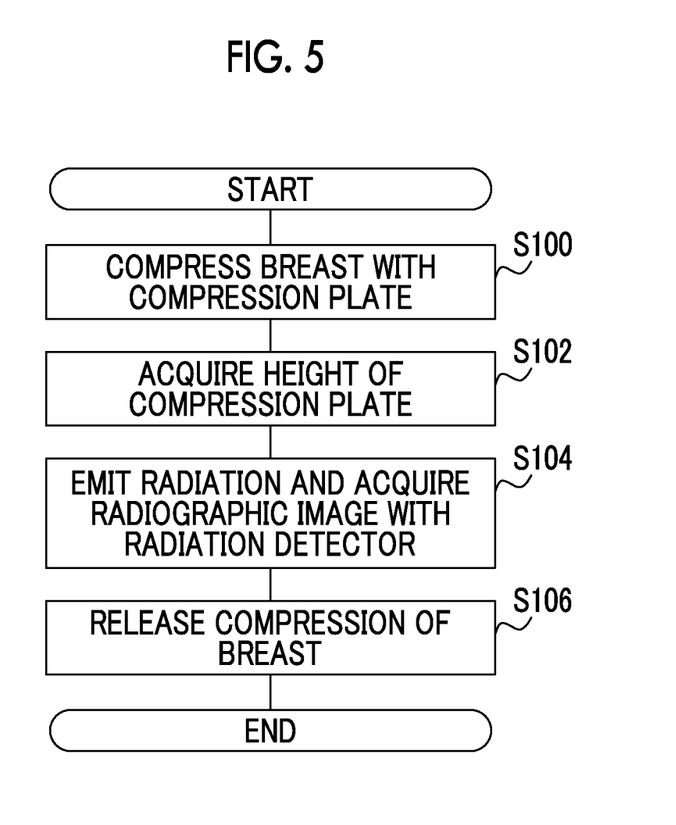
FIG. 5 is a flowchart illustrating an example of the flow of a radiography operation of the mammography apparatus according to the embodiment.

In Step S10 illustrated in FIG. 4, the mammography apparatus 10 captures a radiographic image in response to a command input from the user through the console 6. In a case in which the user positions the subject, the mammography apparatus 10 starts a radiography operation in response to a command from the user. FIG. 5 is a flowchart illustrating an example of the flow of the radiography operation in the mammography apparatus 10 according to this embodiment.

In Step S100 illustrated in FIG. 5, the control unit 30 compresses the breast placed on the imaging surface 24 of the imaging table 16 with the compression plate 20.

In a case in which the breast is compressed and fixed by the compression plate 20, in Step S102, the control unit 30 acquires the height of the compression plate 20, specifically, the distance between the imaging surface 24 and the compression plate 20. A method for acquiring the height of the compression plate 20 in the control unit 30 is not particularly limited. For example, the control unit may detect the amount of movement of the compression plate 20 from a predetermined initial position in order to compress the breast and acquire the height of the compression plate 20 on the basis of the initial position and the amount of movement. In the radiography system 1 according to this embodiment, the height of the compression plate 20 in imaging is regarded as the thickness of the breast in imaging.

Then, in Step S104, the control unit 30 directs the radiation source 29 to irradiate the breast of the subject with the radiation X in response to a command from the user and directs the radiation detector 11 to capture the radiographic image of the breast. In addition, the image data of the radiographic image captured by the radiation detector 11 is transmitted to the console 6 in a state in which it is associated with information indicating the height of the compression plate 20 at a predetermined time, such as the time immediately after the imaging ends or the time when image data is received from the console 6.

Then, in Step S106, the control unit 30 releases the compression of the breast by the compression plate 20. Specifically, the control unit 30 moves the compression plate 20 in a direction in which the compression plate 20 becomes far away from the imaging table 16 (a direction in which the compression plate 20 becomes close to the radiation source 29) to release the compression of the breast. The radiography operation of the mammography apparatus 10 is ended by the end of this step.

The radiographic image captured in Step S10 may be any image corresponding to, for example, an imaging order or a command from the user and may be one or both of a CC image and an MLO image.

In a case in which the capture of the radiographic image in Step S10 (see FIG. 4) ends in this way, in Step S12, the console 6 performs a mammary gland percentage derivation process, whose example will be described with reference to FIG. 6, to derive the percentage of the mammary glands of the breast from the radiographic image. Then, the imaging operation in the entire radiography system 1 ends.

As described above, the console 6 according to this embodiment has a function of deriving the percentage of the mammary glands of the breast from the radiographic image of the breast. Here, the principle of deriving the percentage of the mammary glands of the breast from the radiographic image will be described. The percentage of the mammary glands means the volume ratio of the mammary gland tissues to the breast tissues. The percentage of the mammary glands indicates the percentage of the mammary glands in a thickness direction of the breast which is the emission direction of the radiation X. In a case in which there are no mammary glands and only fat is present, the percentage of the mammary glands is 0. As the density of the mammary glands becomes higher, the percentage of the mammary glands becomes higher.

Figure 7:
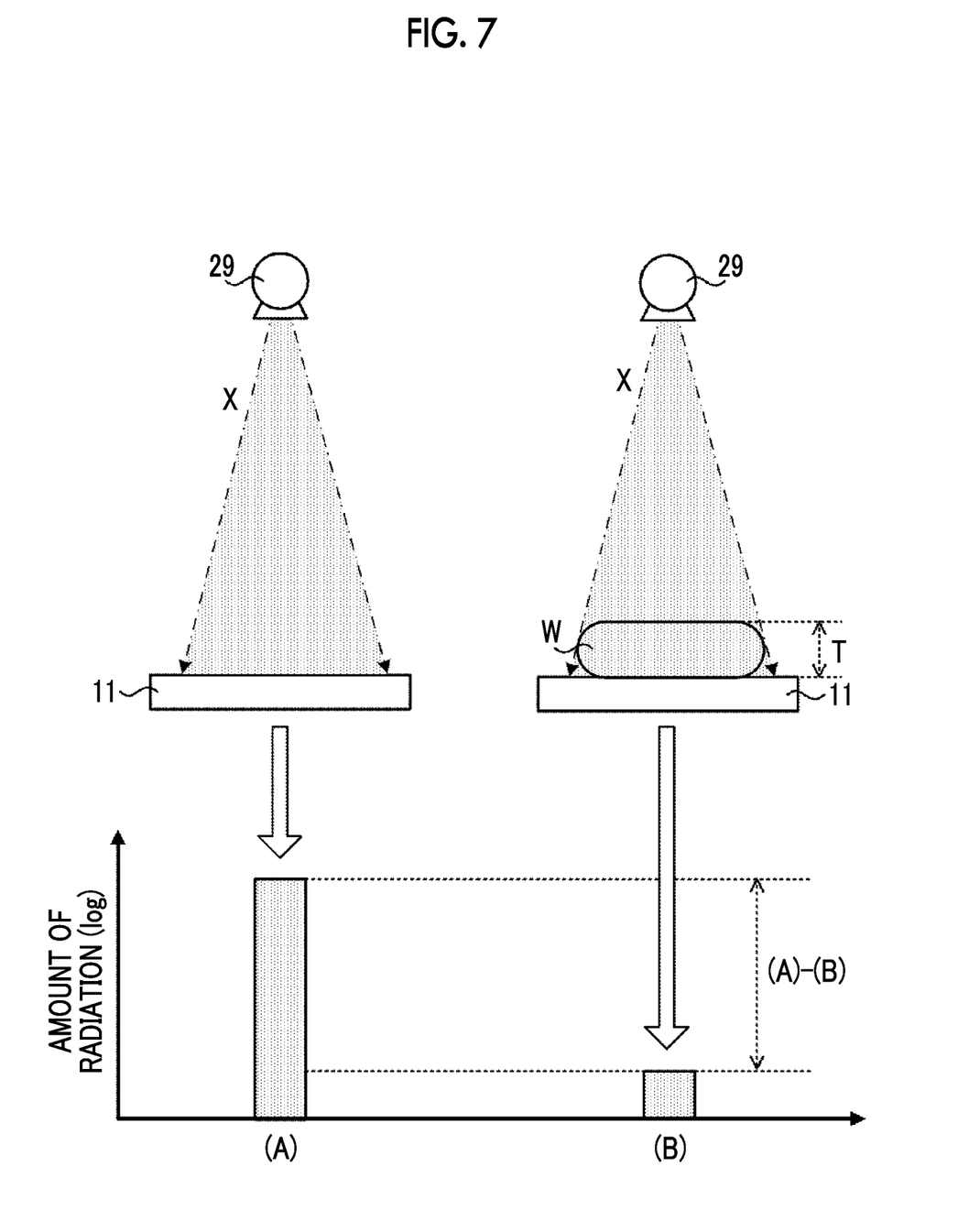
FIG. 7 is a diagram schematically illustrating the principle of deriving the percentage of the mammary glands in the embodiment.

As illustrated in FIG. 7, since the radiation X passes through the breast which is an object W and is attenuated, the amount of radiation reaching the radiation detector 11 (hereinafter, referred to as "the amount of incident radiation") varies. In FIG. 7, (A) schematically illustrates a case in which the radiation X emitted from the radiation source 29 directly reaches the radiation detector 11 without passing through the breast and (B) schematically illustrates a case in which the radiation X emitted from the radiation source 29 passes through the breast and reaches the radiation detector 11. A difference ((A)–(B)) between the amount of incident radiation in the case of (A) and the amount of incident radiation in the case of (B) is equal to the attenuation of the radiation X by the breast. The attenuation of the radiation X by the breast is determined by the thickness T of the breast and the composition (the percentage R of the mammary glands) of the breast. In a case in which the tissues of the breast include the mammary gland tissues and fat tissues, specifically, the attenuation ((A)–(B)) by the breast is derived by the following Expression (1). In the following Expression (1), R indicates the percentage (a numerical value in the range of 0 to 1) of the mammary glands.

$$(A)-(B)=\bar{\mu}_a \times (1-R) \times T + \bar{\mu}_g \times R \times T \tag{1}$$

$\bar{\mu}_a$: an attenuation coefficient of the fat tissue
$\bar{\mu}_g$: an attenuation coefficient of the mammary gland tissue
In the above-mentioned Expression (1), $\bar{\mu}_a \times (1-R) \times T$ indicates the attenuation of the radiation X by the fat tissues.

In addition, $\bar{\mu}_g \times R \times T$ indicates the attenuation of the radiation X by the mammary gland tissues.

The percentage R of the mammary glands is derived for each pixel of the radiographic image (breast image) by the following Expression (2) from the above-mentioned Expression (1).

$$R = \frac{\log I_0 - \log I_1 - \bar{\mu}_a \times T}{(\bar{\mu}_g - \bar{\mu}_a) \times T} \tag{2}$$

In the above-mentioned Expression (2), $I_0$ is the amount of incident radiation on a direct region (so-called directly irradiated region) which is a region corresponding to the radiation X that is directly emitted without passing through the breast in the radiographic image and $I_1$ is the amount of incident radiation on a breast region.

The percentage R of the mammary glands derived for each pixel by the above-mentioned Expression (2) is integrated in the entire breast image (breast region) of the radiographic image to derive the volume of the mammary glands in the entire breast and the percentage of the mammary glands with respect to the volume of the entire breast.

In the above-mentioned Expression (2), the thickness T of the breast is used. However, in many cases, an error is included in the thickness T of the breast acquired in imaging. The size of the error included in the thickness T of the breast is the same regardless of the thickness of the breast. Therefore, as the thickness T of the breast becomes smaller, the influence of the error becomes relatively larger. As a result, there is a concern that the accuracy of the derived percentage of the mammary glands will be reduced.

In a case in which the amount of incident radiation on a fat tissue pixel obtained by a portion of the breast which is estimated to be composed of only the fat tissues in the breast image of the radiographic image of the breast is A, the relationship represented by the following Expression (3) is established between the amount of incident radiation A and the thickness of the breast. In this embodiment, a value obtained by performing log conversion for the amount of incident radiation A is the value of a corresponding fat tissue pixel. The term "fat tissue pixel" is a pixel corresponding to a portion of the breast which is estimated to be composed of only the fat tissues. For example, the "fat tissue pixel" may be a pixel corresponding to a portion of the breast in which the percentage of the fat tissues is higher than that of at least the mammary gland tissues and is greater than a predetermined threshold value for regarding a portion of the breast as being composed of only the fat tissues.

$$\log A = \log I_0 - \overline{\mu}_a \times T \qquad (3)$$

In a case in which the above-mentioned Expression (3) is substituted into the above-mentioned Expression (2), the following Expression (4) is obtained. The derivation of the percentage R of the mammary glands by the following Expression (4) is less affected by the thickness T of the breast than the derivation of the percentage R of the mammary glands by the above-mentioned Expression (2).

$$R = \frac{\log A - \log I_1}{\overline{\mu}_g - \overline{\mu}_a} \times \frac{1}{T} \qquad (4)$$

The method disclosed in JP2010-253245A derives the percentage R of the mammary glands using the following Expression (5) obtained by estimating the thickness T of the breast from the above-mentioned Expression (3). According to the following Expression (5), for a portion (pixel) including the largest number of fat tissues, R=0 (0%) is derived as the percentage of the mammary glands.

$$R = \frac{\log A - \log I_1}{\log I_0 - \log A} \times \frac{1}{\overline{\mu}_g / \overline{\mu}_a - 1} \qquad (5)$$

According to the above-mentioned Expression (5), it is possible to derive the percentage R of the mammary glands without using the thickness T of the breast. Therefore, the derivation of the percentage R of the mammary glands by the above-mentioned Expression (5) is less affected by the thickness T of the breast than the derivation of the percentage R of the mammary glands by the above-mentioned Expression (1) and the derivation of the percentage R of the mammary glands by the above-mentioned Expression (2). As a result, in a case in which the percentage R of the mammary glands is derived using the above-mentioned Expression (5), it is possible to prevent a reduction in the accuracy of deriving the percentage of the mammary glands due to the error included in the thickness T of the breast.

In the method for deriving the percentage of the mammary glands using the above-mentioned Expression (5), the value of the fat tissue pixel is used. In a case in which no fat tissue pixels are included in the breast image, there is a concern that the accuracy of deriving the percentage of the mammary glands will be reduced. For example, for the type of breast, a fatty type, a mammary gland scattered type, a non-uniform high-concentration type, and a high-concentration type are generally known. Among these types, in the high-concentration type, that is, a so-called dense breast, the fat tissue pixels have a higher tendency not to be included in the breast image than those in other types.

In a case in which the type of breast is the high-concentration type, while the fat tissue pixel is likely not to be included in the breast image, a mammary gland tissue pixel obtained by a portion of the breast which is estimated to be composed of only the mammary gland tissues is likely to be included in the breast image. Here, the term "mammary gland tissue pixel" is a pixel corresponding to a portion of the breast which is estimated to be composed of only the mammary gland tissues. For example, the "mammary gland tissue pixel" may be a pixel corresponding to a portion of the breast in which the percentage of the mammary gland tissues is higher than that of at least the fat tissues and is greater than a predetermined threshold value for regarding a portion of the breast as being composed of only the mammary gland tissues.

In a case in which the amount of incident radiation on the mammary gland tissue pixel is G, the relationship represented by the following Expression (6) is established between the amount of incident radiation G and the thickness of the breast. Therefore, in a case in which the type of breast is the high-concentration type, it is preferable to derive the percentage R of the mammary glands using the following Expression (7) obtained by estimating the thickness T of the breast from the following Expression (6). According to the following Expression (7), for a portion (pixel) including the largest number of mammary gland tissues, R=1 (100%) is derived as the percentage of the mammary glands.

$$\log G = \log I_0 - \overline{\mu}_g \times T \qquad (6)$$

$$R = \frac{1}{1 - \overline{\mu}_a / \overline{\mu}_g} \times \frac{\log I_0 - \log I_1}{\log I_0 - \log G} - \frac{1}{\overline{\mu}_g / \overline{\mu}_a - 1} \qquad (7)$$

Even in a case in which the above-mentioned Expression (7) is used, it is possible to derive the percentage R of the mammary glands without using the thickness T of the breast. Therefore, the derivation of the percentage R of the mammary glands by the above-mentioned Expression (7) is less affected by the thickness T of the breast than the derivation of the percentage R of the mammary glands by the above-mentioned Expression (1) and the derivation of the percentage R of the mammary glands by the above-mentioned Expression (2). As a result, in a case in which the percentage R of the mammary glands is derived using the above-mentioned Expression (7), it is possible to prevent a reduction in the accuracy of deriving the percentage of the mammary glands due to the error included in the thickness T of the breast.

As described above, as the thickness of the breast becomes smaller, the accuracy of deriving the percentage of the mammary glands becomes lower due to the error included in the thickness T of the breast. Therefore, the console 6 according to this embodiment derives the percentage R of the mammary glands with the above-mentioned Expression (5) or (7) without using the thickness T of the breast in a case in which the thickness of the breast is small and derives the percentage R of the mammary glands with the above-mentioned Expression (2) or (4) using the thickness T of the breast in a case in which the thickness of the breast is large.

Next, the mammary gland percentage derivation process performed by the console 6 will be described with reference to FIG. 6. FIG. 6 is a flowchart illustrating an example of the flow of the mammary gland percentage derivation process performed by the control unit 40 of the console 6 according to this embodiment.

Figure 6:
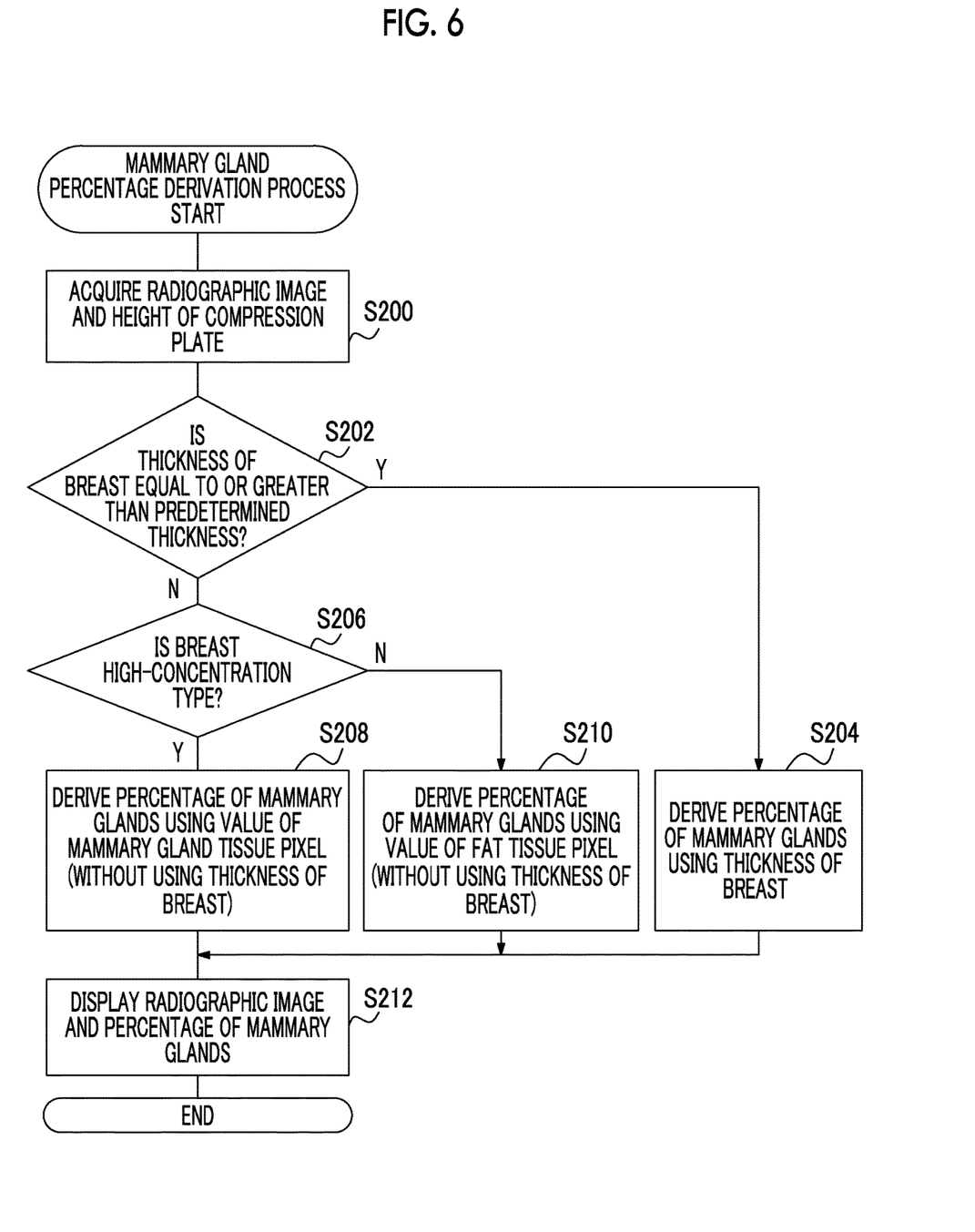
FIG. 6 is a flowchart illustrating an example of the flow of a mammary gland percentage derivation process performed by the console according to the embodiment.

For example, in a case in which the mammography apparatus 10 ends the capture of the radiographic image (Step S10 in FIG. 4), in the console 6 according to this embodiment, the CPU 40A of the control unit 40 executes a mammary gland percentage derivation processing program stored in the ROM 40B to perform the mammary gland percentage derivation process illustrated in FIG. 6. In a case in which the mammary gland percentage derivation process is performed, the control unit 40 functions as an example of an acquisition unit and a derivation unit according to the present disclosure.

As illustrated in FIG. 6, in Step S200, the control unit 40 acquires the radiographic image captured in Step S10 and the height of the compression plate 20. Specifically, the control unit 40 acquires image data of the radiographic image and information indicating the height of the compression plate 20 associated with the image data of the radiographic image. In addition, the acquisition destination of the radiographic image is not particularly limited as long as it is, for example, a device in which a desired radiographic image is stored and may be, for example, any one of the mammography apparatus 10 or the storage unit 42 of the host apparatus. In this embodiment, the height of the compression plate acquired in this step corresponds to the thickness T of the breast.

Then, in Step S202, the control unit 40 determines whether the thickness T of the breast is equal to or greater than a predetermined thickness (the thickness of the breast the predetermined thickness). The predetermined thickness may be predetermined to be a thickness corresponding to the error included in the thickness T of the breast, specifically, a thickness at which the error is regarded as not affecting the accuracy of deriving the percentage of the mammary glands.

In a case in which the thickness T of the breast is equal to or greater than the predetermined thickness, the determination result in Step S202 is "Yes" and the control unit 40 proceeds to Step S204.

In Step S204, the control unit 40 derives the percentage of the mammary glands using the thickness T of the breast and then proceeds to Step S212. Specifically, the control unit 40 derives the percentage R of the mammary glands using the above-mentioned Expression (2) or the above-mentioned Expression (4). Whether to apply the above-mentioned Expression (2) or the above-mentioned Expression (4) may be predetermined or may be determined in response to, for example, a command from the user. The control unit 40 may apply the above-mentioned Expression (4) in a case in which the amount of incident radiation A on the fat tissue pixel is obtained and may apply the above-mentioned Expression (2) in a case in which the amount of incident radiation A on the fat tissue pixel is not obtained. As described above, the above-mentioned Expression (4) is less affected by the error in the thickness T of the breast than the above-mentioned Expression (2). Therefore, it is preferable to apply the above-mentioned Expression (4) rather than the above-mentioned Expression (2).

In a case in which the above-mentioned Expression (4) is applied, first, the control unit 40 detects the fat tissue pixel included in the breast image of the radiographic image. A method for detecting the fat tissue pixel is not particularly limited. For example, the technique disclosed in JP2010-253245A may be used to detect the fat tissue pixel. In a case in which the technique disclosed in JP2010-253245A is used, first, a radiographic image is divided into a breast image and a direct region. Then, a pectoralis major region in the breast image is extracted. The pectoralis major region is removed from the breast image. Then, a pixel that transmits the largest amount of radiation X in the breast image from which the pectoralis major region has been removed is detected as the fat tissue pixel.

On the other hand, in a case in which the thickness T of the breast is greater than the predetermined thickness, the determination result in Step S202 is "No" and the control unit 40 proceeds to Step S206.

Then, in Step S206, the control unit 40 determines whether the type of breast is the high-concentration type. A method for determining whether the type of breast is the high-concentration type in the control unit 40 is not particularly limited. For example, a method may be used which detects a breast region and a skin line from a breast image, calculates a first index value indicating the degree of a single composition of the breast region, detects the boundary between the fat tissues and the mammary gland tissues in a predetermined range from the skin line to the breast region in the breast image, calculates a second index value indicating the degree of the clogging of the mammary glands with respect to the breast region on the basis of at least one of the strength of the boundary or the distance from the skin line, and identifies the type of breast on the basis of the first index value and the second index value.

For example, the control unit 40 may perform the determination using the technique disclosed in JP1999-019077A (JP-H11-019077A). The technique disclosed in JP1999-019077A (JP-H11-019077A) derives a histogram of the pixel values of the breast image of the radiographic image and classifies the type of breast on the basis of the shape of the derived histogram.

In a case in which the type of breast is not the high-concentration type, that is, a so-called dense breast, the determination result in Step S206 is "Yes" and the control unit 40 proceeds to Step S208.

In Step S208, the control unit 40 derives the percentage of the mammary glands using the value of the mammary gland tissue pixel, without using the thickness T of the breast, and proceeds to Step S212. Specifically, the control unit 40 detects the mammary gland tissue pixel included in the breast image of the radiographic image and derives the percentage R of the mammary glands on the basis of the value of the detected mammary gland tissue pixel, using the above-mentioned Expression (7).

A method for detecting the mammary gland tissue pixel from the breast image in the control unit 40 is not particularly limited. For example, the technique disclosed in JP2010-253245A may be used to detect the mammary gland tissue pixel. In a case in which the technique disclosed in JP2010-253245A is used, first, a radiographic image is divided into a breast image and a direct region. Then, a pectoralis major region in the breast image is extracted. The pectoralis major region is removed from the breast image. Then, a pixel that transmits the smallest amount of radiation X in the breast image from which the pectoralis major region has been removed is detected as the mammary gland tissue pixel.

In this embodiment, the percentage of the mammary glands in the entire breast is derived. However, the invention is not limited to this embodiment. For example, the percentage of the mammary glands may be derived in a portion of the breast, such as a portion in which the density of the mammary glands seems to be high or a portion in which the density of the mammary glands seems to be low.

On the other hand, in a case in which the type of breast is not the high-concentration type, that is, a so-called dense breast, the determination result in Step S206 is "No" and the control unit 40 proceeds to Step S210.

In Step S210, the control unit 40 derives the percentage of the mammary glands using the value of the fat tissue pixel and proceeds to Step S212. Specifically, the control unit 40 detects the fat tissue pixel included in the breast image of the radiographic image and derives the percentage R of the mammary glands on the basis of the value of the detected fat tissue pixel, using the above-mentioned Expression (7).

In Step S212, the control unit 40 displays the radiographic image and the derived percentage of the mammary glands on the display unit 46 and then ends the mammary gland percentage derivation process.

Figure 8:
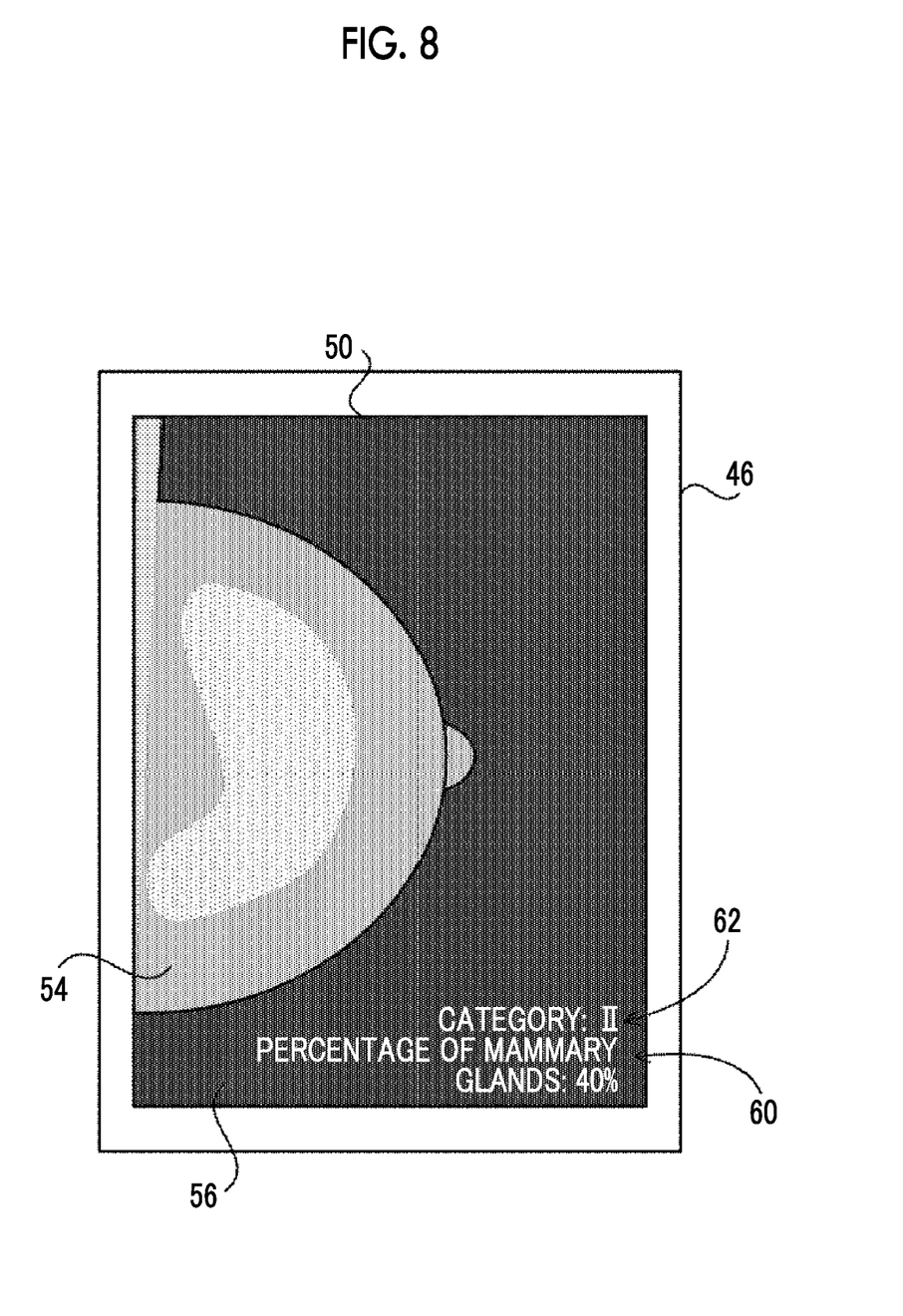
FIG. 8 is a diagram illustrating an example of the display of, for example, a radiographic image on a display unit by the console according to the embodiment.

In addition, the control unit 40 may determine which of predetermined categories classified on the basis of the percentage R of the mammary glands derived in any one of Step S204, Step S208, or Step S210 the breast belongs to and may display the category in addition to the percentage of the mammary glands. In this case, the "category" may be the same as or different from the type of breast. The criteria for determining the category are not particularly limited. For example, in a case in which the percentage of the mammary glands in the entire breast and the percentage of the mammary glands in a portion of the breast are derived, the category classified according to a combination thereof may be used. FIG. 8 illustrates an example of the display of the radiographic image, information indicating the percentage of the mammary glands, and information indicating the category on the display unit 46 by the control unit 40 in this case. FIG. 8 illustrates an example in which a radiographic image 50 includes a breast image 54 and a direct region (an image of the direct region) 56 and information 60 indicating the percentage of the mammary glands and information 62 indicating the category are displayed in the direct region 56 of the radiographic image 50 so as to be superimposed on the direct region 56.

As described above, in the console 6 according to this embodiment, the control unit 40 functions as an acquisition unit that acquires a radiographic image of the breast and information indicating the thickness of the breast in the capture of the radiographic image and a derivation unit that derives the percentage of the mammary glands of the breast image in the radiographic image acquired by the acquisition unit using different methods in a case in which the thickness T of the breast is equal to or greater than a predetermined thickness and a case in which the thickness T of the breast is less than the predetermined thickness.

In the console 6 according to this embodiment, as described above, an error is included in the thickness T of the breast and the influence of the error becomes larger as the thickness T of the breast becomes smaller. Therefore, the console 6 according to this embodiment changes a method for deriving the percentage of the mammary glands according to the thickness T of the breast. The console 6 derives the percentage of the mammary glands using a derivation method that can reduce the influence of the error included in the thickness T of the breast as the thickness T of the breast is reduced.

Therefore, according to the console 6 of this embodiment, it is possible to derive the percentage of the mammary glands with high accuracy, regardless of the thickness of the breast.

Figure 9:
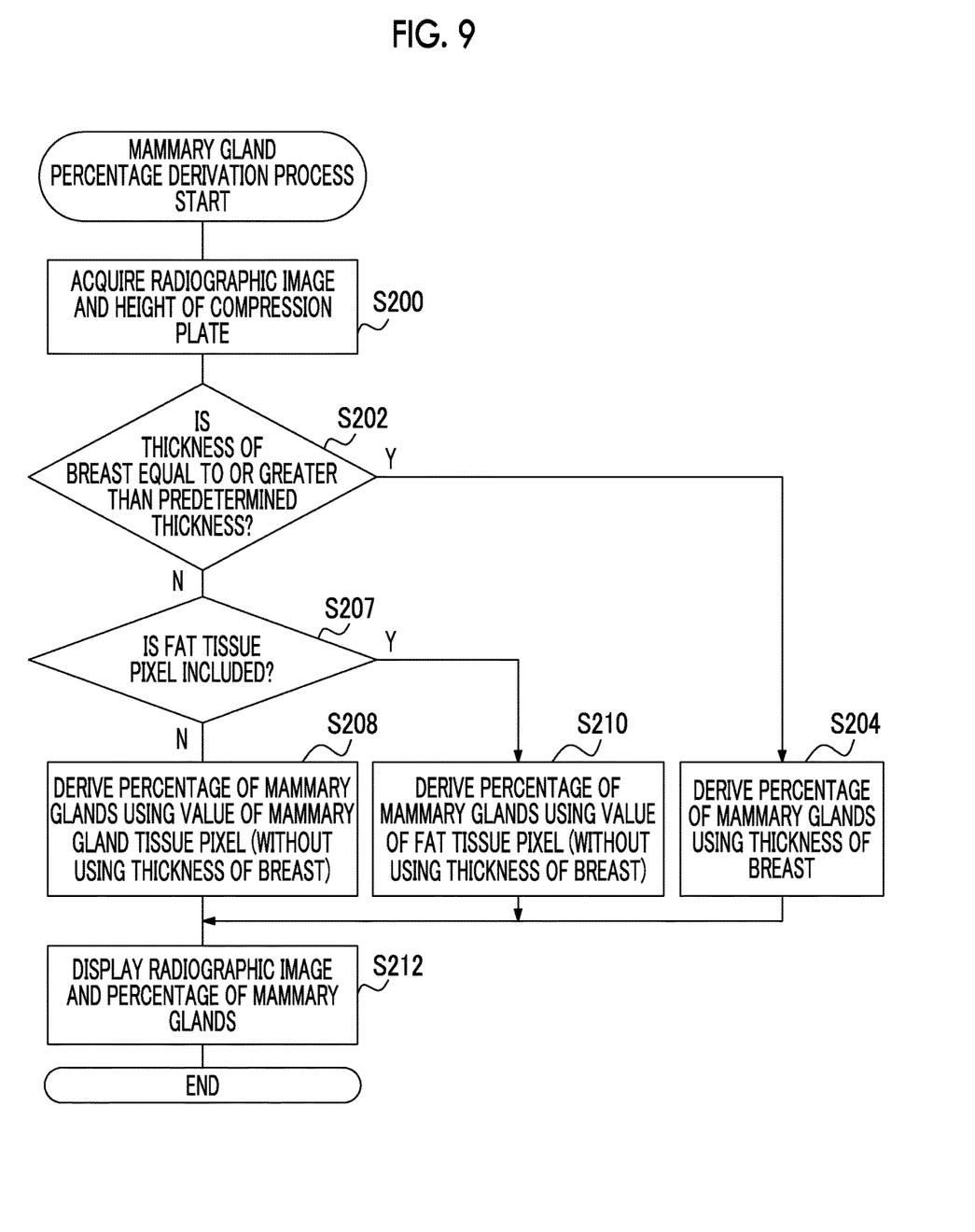
FIG. 9 is a flowchart illustrating another example of the flow of the mammary gland percentage derivation process performed by the console according to the embodiment.

In the mammary gland percentage derivation process performed by the console 6 according to this embodiment, in a case in which the breast is determined to be a high-concentration-type breast, that is, a dense breast (in the case of Y in Step S206 of FIG. 6), the value of the mammary gland tissue pixel is used to derive the percentage of the mammary glands. However, the following aspect may be used. Instead of the determination in Step S206, as in Step S207 in another example of the mammary gland percentage derivation process illustrated in FIG. 9, it is determined whether the fat tissue pixel is included in the radiographic image (breast image). In a case in which the fat tissue pixel is not included, the determination result is "No" and the process proceeds to Step S208 to derive the percentage of the mammary glands using the value of the mammary gland tissue pixel. In a case in which the fat tissue pixel is included, the determination result is "Yes" and the process proceeds to Step S210 to derive the percentage of the mammary glands using the value of the fat tissue pixel.

In this embodiment, the height of the compression plate 20 acquire in the capture of the radiographic image is used as the thickness T of the breast. However, the thickness T of the breast is not limited to this embodiment. For example, a distance sensor may be provided in the imaging table 16 of the mammography apparatus 10. The distance between the compression plate 20 and the imaging surface 24 in a state in which the breast is compressed by the compression plate 20 may be detected by the distance sensor. Then, the detected distance may be applied as the thickness T of the breast.

In this embodiment, it is determined whether to apply the thickness T of the breast to derive the percentage of the mammary glands on the basis of the predetermined thickness. That is, anyone of the two derivation methods is applied on the basis of the thickness T of the breast. However, the invention is not limited to this embodiment. For example, any one of three or more derivation methods may be applied on the basis of the thickness T of the breast. For example, in a case in which the thickness T of the breast is very small, the percentage R of the mammary glands may be derived using the above-mentioned Expression (5) or the above-mentioned Expression (7). In a case in which the thickness T of the breast is greater than that and is medium, the percentage R of the mammary glands may be derived using the above-mentioned Expression (4). In a case in which the thickness T of the breast is greater than the medium thickness and is very large, the percentage R of the mammary glands may be derived using the above-mentioned Expression (2).

In the above-described embodiment, various processors other than the CPU may perform the mammary gland percentage derivation process performed by the execution of software (program) by the CPU. In this case, examples of the processor include a programmable logic device (PLD), such as a field-programmable gate array (FPGA), whose circuit configuration can be changed after manufacture and a dedicated electric circuit, such as an application specific integrated circuit (ASIC), which is a processor having a dedicated circuit configuration designed to perform a specific process. In addition, the mammary gland percentage derivation process may be performed by one of the various processors or may be performed by a combination of two or more processors of the same type or different types (for example, a combination of a plurality of FPGAs and a combination of a CPU and an FPGA). Specifically, the hardware structure of the various processors is an electric circuit obtained by combining circuit elements such as semiconductor elements.

In the above-described embodiment, the aspect in which various programs, such as the programs stored in the control unit 30 of the mammography apparatus 10 and the mammary gland percentage derivation processing program stored in the control unit 40 of the console 6, are stored (installed) in the ROMs (30B and 40B) of the control unit 30 and the control unit 40 in advance has been described. However, the invention is not limited thereto. Each of the various programs may be recorded on a recording medium, such as a compact disk read only memory (CD-ROM), a digital versatile disk read only memory (DVD-ROM), or a universal serial bus (USB) memory, and then provided. In addition, each of the various programs may be downloaded from an external apparatus through the network.

In the above-described embodiment, the radiation X is not particularly limited. For example, X-rays or γ-rays may be applied.

In addition, for example, the configuration and operation of the radiography system 1, the console 6, and the mammography apparatus 10 according to the above-described embodiment are illustrative and may be changed according to the situation, without departing from the scope and spirit of the invention. In addition, the above-described embodiments may be appropriately combined with each other.

What is claimed is:

1. An image processing apparatus comprising a processor coupled to a memory, the processor being configured to:
   acquire a radiographic image of a breast and information indicating a thickness of the breast in capture of the radiographic image; and
   derive a percentage of mammary glands of a breast image in the radiographic image acquired by the acquisition unit using different methods in a case in which the thickness of the breast is equal to or greater than a predetermined thickness and a case in which the thickness of the breast is less than the predetermined thickness.

2. The image processing apparatus according to claim 1, wherein, in a case in which the thickness of the breast is equal to or greater than the predetermined thickness, the processor is configured to derive the percentage of the mammary glands of the breast image on the basis of the thickness of the breast.

3. The image processing apparatus according to claim 1, wherein, in a case in which the thickness of the breast is less the predetermined thickness, the processor is configured to derive the percentage of the mammary glands of the breast image on the basis of an amount of incident radiation on a fat tissue pixel obtained by a portion of the breast which is estimated to be composed of only fat tissues in the radiographic image or an amount of incident radiation on a mammary gland tissue pixel obtained by a portion of the breast which is estimated to be composed of only mammary gland tissues in the radiographic image.

4. The image processing apparatus according to claim 3, wherein, in a case in which a type of the breast is a high-concentration type, the processor is configured to derive the percentage of the mammary glands of the breast image on the basis of the amount of incident radiation on the mammary gland tissue pixel.

5. The image processing apparatus according to claim 3, wherein, in a case in which the type of the breast is a type other than a high-concentration type, the processor is configured to derive the percentage of the mammary glands of the breast image on the basis of the amount of incident radiation on the fat tissue pixel.

6. The image processing apparatus according to claim 1, wherein the predetermined thickness is a thickness corresponding to an error which is included in a measured value of the thickness of the breast.

7. The image processing apparatus according to claim 1, wherein the information indicating the thickness of the breast is information indicating a height of a compression plate that compresses the breast in a case in which an image of the breast is captured.

8. The image processing apparatus according to claim 1, wherein the processor is configured to derive the percentage of the mammary glands for each pixel.

9. An image processing method comprising:
   acquiring a radiographic image of a breast and information indicating a thickness of the breast in capture of the radiographic image; and
   deriving a percentage of mammary glands of a breast image in the radiographic image using different methods in a case in which the thickness of the breast is equal to or greater than a predetermined thickness and a case in which the thickness of the breast is less than the predetermined thickness.

10. A non-transitory recording medium recording an image processing program that is executable by a computer to perform a process comprising:
    acquiring a radiographic image of a breast and information indicating a thickness of the breast in capture of the radiographic image; and
    deriving a percentage of mammary glands of a breast image in the radiographic image using different methods in a case in which the thickness of the breast is equal to or greater than a predetermined thickness and a case in which the thickness of the breast is less than the predetermined thickness.

* * * * *